United States Patent [19]

Stewart et al.

[11] Patent Number: 4,723,538

[45] Date of Patent: Feb. 9, 1988

[54] PENILE CONSTRICTOR RING

[76] Inventors: Edward T. Stewart, 107 Plaza Ter., Dodge City, Kans. 67801; Kenneth W. Slattery, 2411 Buttercup, Richardson, Tex. 75081

[21] Appl. No.: 919,444

[22] Filed: Oct. 16, 1986

[51] Int. Cl.⁴ .............................................. A61F 5/41
[52] U.S. Cl. ..................................................... 128/79
[58] Field of Search .................. 128/79, 327, DIG. 25

[56] References Cited

U.S. PATENT DOCUMENTS

| | | | |
|---|---|---|---|
| 2,614,565 | 10/1952 | Packer | 128/327 |
| 2,839,062 | 6/1958 | Jordan | 128/327 |
| 3,495,589 | 2/1970 | Clement | 128/79 |
| 3,854,469 | 12/1974 | Giori et al. | 128/DIG. 25 |

Primary Examiner—Gene Mancene
Assistant Examiner—Cary E. Stone
Attorney, Agent, or Firm—John A. Hamilton

[57] ABSTRACT

A constrictor ring for the treatment and alleviation of impotence in males consisting of a ring-shaped elastic member operable to encircle the penis adjacent the user's torso, and including operating mechanism to expand it radially inwardly to engage and constrict the penis to inhibit the circulation of blood therein, thereby to encourage or maintain erection of the organ. The mechanism also includes devices for adjustably limiting the degree of constriction to which the organ may be subjected, for instantly removing all constriction if the user should feel pain or discomfort, and most importantly, for automatically releasing all constriction after a predetermined time delay sufficient to allow completion of an act of coitus, this release requiring no conscious act by the user, in order to avoid damage to the organ which otherwise could result if the user shold fall asleep or otherwise fail to release the ring.

12 Claims, 4 Drawing Figures

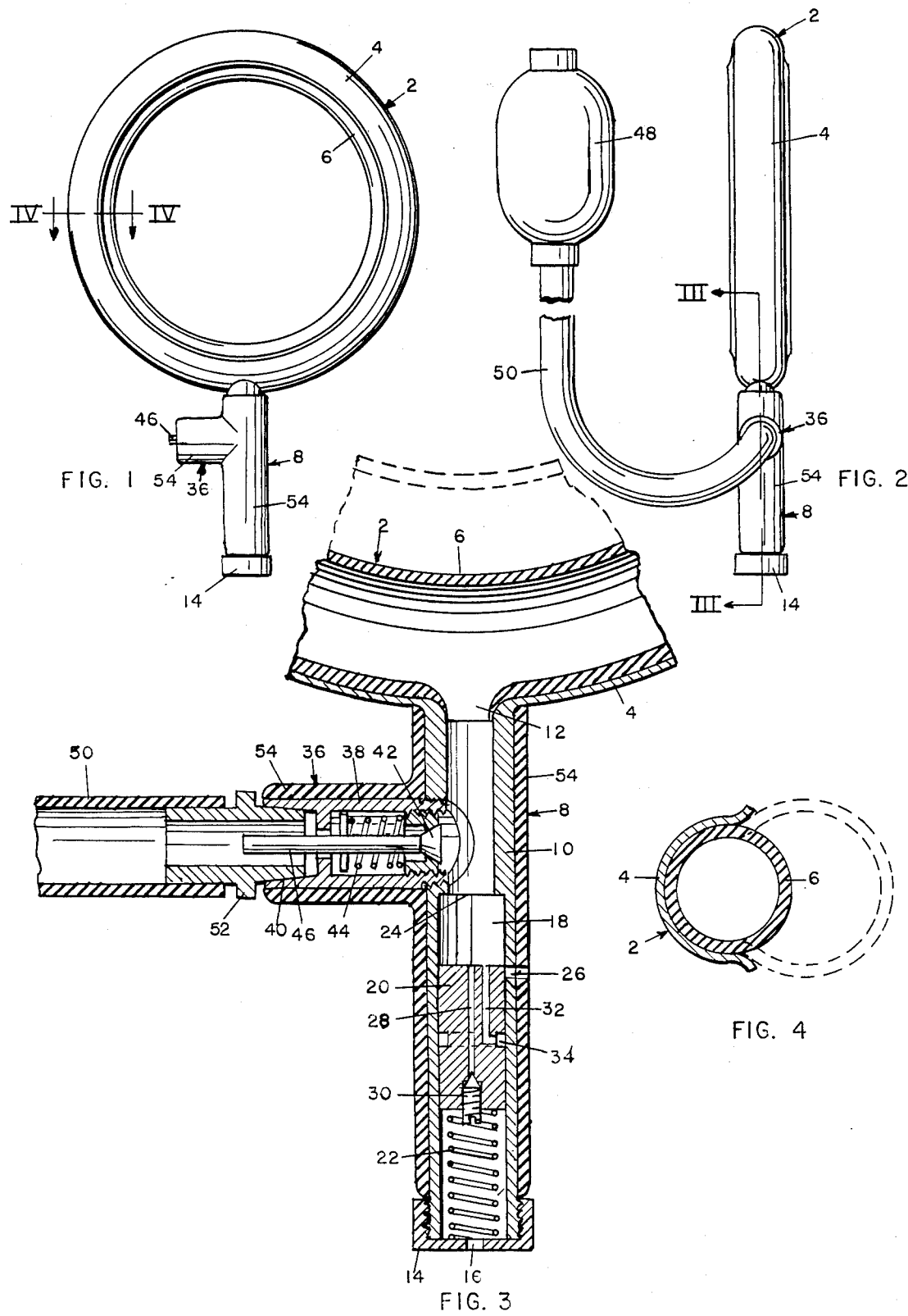

PENILE CONSTRICTOR RING

This invention relates to new and useful improvements in devices for aiding in the treatment and alleviation of impotence in males, and has particular reference to penile constrictor rings.

Penile constrictor rings are ring-shaped devices adapted to be placed in encircling relation to the penis of a user, closely adjacent his torso, and being either tensioned, or adapted to be tensioned, to constrict the penis sufficiently to inhibit the circulation of blood therein. This encourages the formation of an erection of the penis by leaving the blood-supplying arteries, which are relatively deeply embedded in the flesh, relatively unrestricted, while at the same time severely restricting the veins carrying blood away from the organ and disposed caparatively near the surface. Blood is thus trapped in the organ, and erection results. Constrictor rings may be used either alone, or preferably in conjunction with other means for producing the erection, whereby better to retain the erection produced by the other means. One such other device constitutes a rigid chamber adapted to be placed in enclosing relation to the penis, and means for sealing said chamber and pumping air therefrom to form a vacuum.

However, while constrictor rings in general are reasonably effective for their intended purposes in a great number of cases, their use is limited, and often not recommended despite their effectiveness, due to certain dangers to the user if not properly provided with safety devices. Most importantly, the user, in the languor and drowsiness normally following coitus, may fall asleep with the constrictor ring still in place and operative to inhibit blood circulation in the organ, resulting in time in permanent mortification of the flesh, and in extreme cases in permanent damage to or even actual loss of the organ itself.

Accordingly, the principal object of the present invention is the provision of a penile constrictor ring which, while fully effective to inhibit the blood circulation as described, is provided with means operable automatically, after a predetermined time lapse and without conscious action of the user, to release the constriction fully and completely, whereby to allow resumption of normal blood circulation in the organ and thus to avoid such damage.

Another object is the provision of a constrictor ring of the character described wherein the ring is operable by pneumatic inflation thereof to constrict the penis, but is provided with a small, controlled vent to atmosphere whereby said constriction is gradually reduced.

A further object is the provision of a constrictor ring of the character described above wherein the inflating pressure is gradually reduced from one level to another, both levels being within a range determined by competent medical authority to be effective for the purpose of maintaining an erection, and then reduced to zero substantially instantly.

A still further object is the provision of a constrictor ring of the character described having adjustable means for automatically limiting the degree of air pressure in the ring, and also for adjusting the rate of air leakage therefrom. General safety requires limitation of the air pressure, and the time of constriction is a function of said air pressure and the rate of controlled leakage.

Other objects are simplicity and economy of construction, and ease, dependability and reliability of operation.

With these objects in view, as well as other objects which will appear in the course of the specification, reference will be had to the accompanying drawing, wherein:

FIG. 1 is a front elevational view of a penile constrictor ring embodying the present invention, with the inflating pump omitted, FIG. 2 is a side elevational view of the constrictor ring as shown in FIG. 1, with the inflation pump operably connected thereto, FIG. 3 is an enlarged sectional view taken on line III—III of FIG. 2, and FIG. 4 is an enlarged sectional view of the ring taken on line IV—IV of FIG. 1, showing the ring inflated in dotted lines.

Like reference numerals apply to similar parts throughout the several views, and the numeral 2 applies generally to a penile constrictor ring embodying the present invention. Said ring includes a generally circular retainer 4 of substantially greater internal diameter than is necessary to encircle even an erect penis, and formed of a suitably sanitary material such as stainless steel. It is of inwardly opening U-shaped channel form in cross-sectional contour. A torus-shaped endless tube 6 is secured within said retainer, and is of such dimensions that when relaxed it fits within retainer 4 snugly as shown in FIGS. 1 and 3, and in solid lines in FIG. 4. Said tube is formed of elastic material such as latex rubber.

The retainer 4 is provided with a short, radially extending stem 8 projecting outwardly therefrom, said stem including a rigid tube 10, which may also be formed of stainless steel, fixed at its inner end to retainer 4 in communicating relation to the interior thereof, latex tube 6 having an aperture 12 sealed in communicating relation with tube 10, as shown in FIG. 3. Tube 10 is closed at its outer end by a threaded cap 14 having an aperture 16 formed therethrough. The outer end portion of tube 10 forms an interior cylinder 18 in which a piston 20 is slidably movable, said piston being normally biased inwardly in the cylinder by a spring 22 disposed in the cylinder between the piston and cap 14, until it engages an internal shoulder 24 of the cylinder, but being movable outwardly in the cylinder, as shown, by air pressure within the system, until it uncovers a vent hole 26 formed in the side of tube 10. A first passage 28 is formed longitudinally through the piston, and is finely controlled by a needle valve 30 threaded into the outer end of the piston and adjustable by screw driver only when cap 14 has been removed. A second passage 32 interconnects the cylinder inwardly of the piston with a groove 34 formed peripherally in the cylindrical surface of the piston.

Air may be introduced into ring 6 through a side stem 36 including a rigid tube 38 interconnected at its inner end into tube 10 intermediate cylinder 18 and tube 6, and having an outwardly opening tapered socket 40 formed in its outer end. Carried in tube 38 is a check valve 42 biased by a spring 44 to a closed position to prevent escape of air from tube 10, but having a stem 46 extending outwardly from socket 40. The check valve may be opened against the bias of spring 44 by finger pressure on the outer end of the stem.

Pumping means for delivering air to the constrictor ring may constitute an ordinary rubber squeeze bulb 48

(see FIG. 2) fitted with air valves in a manner too old and well known to require detailed description such that repeated squeezing of the bulb will deliver air under pressure through a flexible hose 50, said hose being provided with a tapered tubular end fitting 52 which may be pressed wedgingly and frictionally into socket 40 of tube 38, as shown in FIG. 3. The end fitting may be freed from the socket whenever desired by a slight twisting motion thereof. Stems 8 and 36 may be provided with coverings 54 of latex rubber, if desired, for greater comfort.

In use, retainer 4 and ring 6, with ring 6 deflated, is fitted about the base of the user's penis, closely adjacent his torso. The penis may not be erect, if the constrictor ring is to be used to assist in causing erection, or already erect if the constrictor ring is to be used to assist in maintaining erection for longer periods of time. Squeeze bulb hose 50 is then engaged in socket 40, and bulb 48 squeezed repeatedly to pump air past check valve 42 to inflate the penis encircling ring 6. The check valve opens against spring 44 to admit the air, but closes immediately to retain the air. Tube 6 is thus inflated generally as shown in dotted lines in FIGS. 3 and 4, expanding principally radially inwardly due to the constraining effect of retainer 4, and thus exerts an inward compressive force on the penis, whereby to inhibit the circulation of blood therein as discussed above.

General safety and user welfare requires strict limitation of the compressive force to which the penis is subjected, which in turn requires limitation of air pressure in tube 6. The present structure provides this limitation by the fact that as the pressure rises it forces piston outwardly against spring 22, until the piston uncovers vent hole 26, whereupon any additional air pumped is bled off to atmosphere, and the piston comes to rest at the position shown in FIG. 3, with the piston just covering vent 26. The maximum pressure obtainable, therefore, is determined by the strength of spring 22, and the spring selected for use should be determined by competent medical advice to be according to the requirements and limitations of each individual user.

Air of course immediately starts to leak through piston passage 28, needle valve 30 and cap aperture 16 to atmosphere, and piston 20 therefore is moved gradually inwardly by spring 22 as the ring pressure decreases, until such time as groove 34 of the piston registers with vent hole 26, whereupon the total ring pressure is vented to atmosphere virtually instantaneously, the piston coming to rest against shoulder 24 and the whole system dropping to atmospheric pressure. In a given structure, the time required for the piston to move from the FIG. 3 position to a venting the tube to atmosphere is determined first by the strength of spring 22 and second by the setting of needle valve 30. The function of spring 22 in limiting the maximum pressure in the tube, as already described, is of course important in preventing possible immediate damage to the penis, but the time passing between these two positions of the piston is also very important, and must be limited to prevent possibly permanent damage to the penis, which is the primary object of this invention. A time period of perhaps fifteen minutes is suggested as being long enough to permit coitus, but short enough to prevent damage to the organ. It is generally desirable, moreover, that the tube pressure at both of these positions be within a range sufficiently high to be effective in maintaining erection, but then dropped to zero immediately, as is the case, rather than simply allowing the pressure to drop to zero entirely through the air leakage occurring through valve 30. In the latter case, the pressure might drop very slowly through the lower ranges, not materially assisting in the maintenance of erection but still occupying enough time to be possibly injurious to the penis. If the user feels pain or discomfort at any time, he may press on stem 46 of check valve to relieve all ring pressure instantly.

While we have shown and described a specific embodiment of our invention, it will be readily apparent that many minor changes of structure and operation could be made without departing from the spirit of the invention. It is believed that the basic feature of this invention is the provision of a penile constrictor ring having means whereby it is released after a predetermined time delay, the release means being entirely automatic and requiring no conscious action by the user. Within that broad concept, it will be apparent that ring 6 could be hydraulically as well as air-inflated, so long as a reservoir into which the fluid could leak is provided, that retainer 4, while useful, is not essential, and that the tube 6 could in fact be replaced by a simple elastic band with its ends connected by a releasable latch. The actual timing of the release also need not be by needle valve as shown, but could be performed chemically as for example by chemical destruction of a pressure-retaining diaphragm, or electrically by means of some sort of electric clock mechanism. A microchip timer unit offers many advantages both of extremely accurate timing when necessary, and very low requirements for electric power.

What we claim as new and desire to protect by Letters Patent is:

1. A penile constrictor ring for aiding in the treatment of impotence in males, and comprising:
   a. a ring-shaped member of elastic material adapted to be engaged about the penis in closely adjacent relation to the user's torso,
   b. manually actuated operating means operable when actuated to secure said ring-shaped member in tensioned relation around the penis, whereby to constrict the penis to inhibit the circulation of blood therein, and
   c. release means operable automatically after a predetermined time delay to deactuate said operating means to relieve the penis of constriction, and to maintain said deactuation until said operating means is again manually actuated.

2. A constrictor ring as recited in claim 1 wherein said operating means includes means operable to limit the tension applicable thereby to said ring-shaped member to a predetermined maximum.

3. A constrictor ring as recited in claim 1 wherein said release means includes means operable to adjust the extent of the predetermined time delay which must occur before said release means deactuates said operating means.

4. A constrictor ring as recited in claim 1 with the addition of:
   a. means operable automatically to limit the tension applicable to said ring-shaped member by said operating means, and
   b. means operable to adjust the extent of the predetermined time delay which must occur before said release means deactuates said operating means.

5. A constrictor ring as recited in claim 4 with the addition of manually operable means operable to deactuate said operating means instantaneously at any time, to relieve the penis of constriction.

6. A constrictor ring as recited in claim 1 wherein said ringshaped member constitutes a toroidal ring of elastic material operable to be tensioned to apply constriction to the penis by inflation thereof with a suitable fluid, and wherein said operating means includes pumping means operable to deliver said fluid into said ring.

7. A constrictor ring as recited in claim 6 wherein said operating means additionally includes a relief valve automatically opened at or above a predetermined ring pressure to allow said fluid to escape from said ring.

8. A constrictor ring as recited in claim 6 wherein said release means comprises:
   a. valve means operable to allow a slow, controlled leakage of fluid from said ring, whereby fluid pressure in said ring is gradually reduced, and
   b. valve means responsive to fluid pressure within said ring to vent said ring fully and immediately whenever said fluid pressure drops to a predetermined level.

9. A constrictor ring as recited in claim 6 wherein said toroidal ring is air-inflatable, and wherein said operating means includes an air pump operable to deliver air to said ring.

10. A constrictor ring as recited in claim 6 wherein said operating means and said release means additionally comprise:
    a. a conduit interconnected into said ring, and through which fluid is delivered to said ring,
    b. a check valve interposed in said conduit and operable normally to prevent outward flow of fluid from said ring,
    c. a tubular stem interconnected into said ring, but not through said check valve,
    d. a piston slidably mounted in said stem, and operable to be moved outwardly therein by pressure within said ring,
    e. means providing a passage continuously venting said ring to atmosphere,
    f. a vent valve closely restricting the flow of fluid through said passage to a slow rate, and
    g. a spring yieldably resisting outward movement of said piston responsively to fluid pressure in the ring, said stem being provided with an atmospheric vent operable to be uncovered by said piston when the fluid pressure has risen to a predetermined level and said spring has been compressed to a predetermined tension, said piston having a passage formed there-through operable to interconnect said ring to said atmospheric vent to relieve remaining ring pressure after the piston has been moved inwardly by said spring to a predetermined distance, as allowed by leakage of fluid from said ring through said vent valve.

11. A constrictor ring as recited in claim 10 with the addition of manually operable means for opening said check valve to vent said ring totally to atmosphere and relieve the penis of all constriction virtually instantaneously whenever desired.

12. A constrictor ring as recited in claim 11 with the addition of a substantially rigid retainer ring encircling said toroidal ring in engagement therewith, whereby said toroidal ring is constrained to principally radially inward constriction to better subject the penis to constriction.

* * * * *